US00PP20034P2

(12) United States Plant Patent
Hofmann

(10) Patent No.: US PP20,034 P2
(45) Date of Patent: May 26, 2009

(54) **NEW GUINEA *IMPATIENS* PLANT NAMED 'FISNICS ORGA'**

(50) Latin Name: *Impatiens hawkeri*
Varietal Denomination: Fisnics Orga

(75) Inventor: Birgit Christa Hofmann, Bendorf (DE)

(73) Assignee: Syngenta Participations AG (CH)

( * ) Notice: Subject to any disclaimer, the term of this patent is extended or adjusted under 35 U.S.C. 154(b) by 52 days.

(21) Appl. No.: 12/077,382

(22) Filed: Mar. 19, 2008

(51) Int. Cl.
*A01H 5/00* (2006.01)

(52) U.S. Cl. ..... Plt./318.3
(58) Field of Classification Search ..... Plt./318.3
See application file for complete search history.

*Primary Examiner*—Annette H Para
(74) *Attorney, Agent, or Firm*—S. Matthew Edwards

(57) ABSTRACT

A new New Guinea *Impatiens* plant particularly distinguished by its brilliant orange flower color, large flowers, medium green, smooth and glossy foliage, mounded, bushy, medium-sized plant habit, and early to medium flowering response is disclosed.

1 Drawing Sheet

Genus and species: *Impatiens hawkeri* W. Bull.
Variety denomination: 'Fisnics Orga'.

BACKGROUND OF THE NEW PLANT

The present invention comprises a new and distinct cultivar of New Guinea *Impatiens,* botanically known as *Impatiens hawkeri* W. Bull, and hereinafter referred to by the cultivar name 'Fisnics Orga'. The new cultivar originated from a hybridization made in the summer of 2003 in Hillscheid, Germany. The female parent was the proprietary *Impatiens* plant 'K03-2478-2' (unpatented), while the male parent was the proprietary *Impatiens* plant 'K02-290-2' (unpatented). The seeds produced by the hybridization were sown in a greenhouse in Portugal in the fall of 2003. A single plant selection was chosen for further evaluation and for asexual propagation in March 2004 in Moncarapacho, Portugal.

The new cultivar was created in 2003 in Hillscheid, Germany and has been asexually reproduced repeatedly by vegetative cuttings and tissue culture in Moncarapacho, Portugal and Hillscheid, Germany over a three-year period. 'Fisnics Orga' has not been observed under all possible environmental conditions. The phenotype may vary significantly with variations in environment such as temperature, light intensity and day length, without, however, any variation in genotype. The present invention has been found to retain its distinctive characteristics through successive asexual propagations.

Plant Breeder's Rights for this cultivar were applied for in Canada on Mar. 30, 2007, and in Switzerland on May 23, 2007. 'Fisnics Orga' has not been made publicly available more than one year prior to filing of this application.

SUMMARY OF THE INVENTION

The following are the most outstanding and distinguishing characteristics of this new cultivar when grown under normal horticultural practices in Hillscheid, Germany, and in Langley, British Columbia, Canada.

1. Brilliant orange flower color;
2. Large flowers, weak butterfly-shape;

3. Medium green, smooth and glossy foliage;
4. Mounded, bushy, medium-sized plant habit; and
5. Early to medium flowering response.

DESCRIPTION OF PHOTOGRAPH

This new New Guinea *Impatiens* plant is illustrated by the accompanying photograph which shows overall plant habit including blooms, buds, and foliage of the plant; the colors shown are as true as can be reasonably obtained by conventional photographic procedures. The photograph is of a whole plant about 12 to 14 weeks old, grown in a greenhouse in Hillscheid, Germany, in the late summer of 2006.

DESCRIPTION OF THE NEW CULTIVAR

The following detailed descriptions set forth the distinctive characteristics of 'Fisnics Orga'. The data which defines these characteristics were collected from asexual reproductions carried out in Hillscheid, Germany. The plant history was taken on 10- to 12-week-old plants which were planted as rooted cuttings in 12-cm pots in late February 2007 and then grown in a greenhouse at a minimum temperature of 16° C. No growth regulators were used, nor were the shoot (s) pinched. Color readings were taken under natural light in the greenhouse. Color references are primarily to the R.H.S. Colour Chart of The Royal Horticultural Society of London (R.H.S.) (2001).

DETAILED BOTANICAL DESCRIPTION OF THE NEW PLANT

Classification:
*Family.*—Balsaminaceae.
*Botanical.*—*Impatiens hawkeri* W. Bull.
*Common name.*—New Guinea *Impatiens.*

Parentage:
*Female parent.*—'K03-2478-2' a proprietary orange-flowered New Guinea *Impatiens* plant (unpatented).
*Male parent.*—'K02-290-2', a proprietary orange-flowered New Guinea *Impatiens* plant (unpatented).

Growth:

*Growth and branching habit.*—Medium size, round, bushy, and well-branched; the growth is indeterminate, though weak after the beginning of flowering.

*Height.*—11.5 cm.

*Width.*—26.7 cm.

*Propagation.*—Terminal tips for cuttings.

*Time to produce a finished flowering plant.*—10 weeks for a 12-cm pot.

*Time to initiate and develop roots.*—About 18 days at 22° C.

Branches:

*Average number.*—9.2.

*Length of branches.*—7 cm to 12 cm.

*Internode length.*—2.5 cm to 4 cm.

*Diameter of branches.*—0.7 cm to 1.1 cm.

*Stem color.*—Mainly light green, RHS 143C to RHS 144B with reddish nodes of RHS 179A to RHS 179B or RHS 180A (of somewhat variable intensity).

Leaves:

*Arrangement.*—Primarily in whorls.

*Size.*—Length: 13.0 cm. Width: 4.7 cm.

*Shape.*—Elliptic.

*Margin.*—Slightly serrate, ciliated.

*Apex.*—Acuminate.

*Base.*—Acute.

*Color* (*immature leaves*).—Upper surface: RHS 143B (grass-green). Lower surface: Between RHS 143C and RHS 144C.

*Color* (*mature leaves*).—Upper surface: From RHS 137A to RHS 137B. Lower surface: Near RHS 138B.

*Texture.*—Upper surface glabrous, glossy, smooth; lower surface has protruding veins.

*Venation color.*—Upper surface: Mainly RHS 145C (pale light green) with RHS 179D (pale pink) towards base. Lower surface: RHS 144C (light yellow-green).

*Variegation.*—None.

*Petioles.*—Length: About 2.5 cm. Diameter: 0.3 cm to 0.4 cm. Color: Upper surface: RHS 47C (reddish). Lower surface: RHS 145C (pale green). Texture: Glabrous.

Flower buds:

*Shape.*—Ovoid.

*Size.*—Length: 2.2 cm. Diameter: 1.5 cm.

*Color.*—RHS 40C to RHS 40D (orange).

Inflorescence:

*Blooming habit.*—9 weeks after planting of rooted cuttings.

*Inflorescence type.*—Flowers appear solitary in the leaf axils of the upper nodes of the stems.

*Number of flowers per node.*—6 to 8 in various stages of development.

*Flowering season.*—Continuously, mainly from March to October, depending on light intensity.

*Lastingness of individual blooms.*—About 10 to 12 days (greenhouse, 18° C., in spring).

*Fragrance.*—None.

*Peduncle.*—Color: RHS 145C (light green); slight infusion of anthocyanin, RHS 37B, may occur. Size: Length: 6.0 cm. Diameter: 0.2 cm. Texture: Glabrous, flexible.

Flowers:

*Form of corolla.*—Single-type, 5 petals.

*Shape of corolla.*—Large, weakly zygomorphic, weak butterfly shape, with the petals overlapping.

*Corolla size.*—Length: 8.3 cm. Width: 7.7 cm. Depth: 1.0 cm to 1.5 cm.

Petals:

*Shape.*—Cordate, weakly lobed at the top.

*Apex.*—Emarginate.

*Base.*—Attenuate.

*Margin.*—Entire.

*Size.*—Top: Length: 3.8 cm. Width: 4.8 cm. Lateral: Length: 3.8 cm. Width: 3.9 cm to 4.1 cm. Lower: Length: 4.4 cm to 4.5 cm. Width: 4.3 cm to 4.5 cm.

*Color.*—General color description: Brilliant orange. Upper surface of petals: RHS 40B; may appear slightly deeper, between RHS 40A and RHS 40B, in the middle of the banner petal. Lower surface: RHS 40C to mainly RHS 40D.

*Texture.*—Upper surface: Silky. Lower surface: Smooth.

*Aspect.*—Lateral petals may slant slightly upwards.

Calyx:

*General.*—3 sepals visible, the largest one transformed into the spur, two lateral sepals, with the fourth and fifth fused crestlike with the underside of the banner petal.

*Spur.*—Shape: Downwardly curved Color: RHS 53D (pink). Size: Length: 5.6 cm. Diameter: 0.3 cm at the flower base, 0.5 cm at the tip.

*Lateral sepals.*—Shape: Oval. Length: About 1.0 cm. Width: 0.5 cm. Color: RHS 146B (green).

Reproductive organs:

*Stamens.*—Number: 5. Stamen color (upper surface color): Mainly white, RHS 155C, with an orange-red spot, RHS 40B. Anthers: Fused, hooded. Pollen color: RHS 8D (whitish-yellow).

*Pistils.*—Style and stigma: 5, very short, RHS 150D (pale yellow). Ovary: Length: 0.6 cm. Color: RHS 141A (green).

Fruit and seed set: No seed set observed.

Disease and insect resistance: No particular resistance or susceptibility has been observed.

COMPARISON WITH PARENTAL AND COMMERCIAL CULTIVARS

'Fisnics Orga' differs from the female parent 'K03-2478-2' (unpatented) by having larger flowers and glossier leaves than 'K03-2478-2'.

'Fisnics Orga' differs from the male parent 'K02-290-2' (unpatented), by having a taller plant habit than 'K02-290-2'.

'Fisnics Orga' differs from 'Fisnics Orange' (U.S. Plant Pat. No. 13,225) by having a slightly deeper hue of orange flower color and more attractive foliage with flatter, smoother leaf blades and more glossy surface than 'Fisnics Orange'.

'Fisnics Orga' differs from the commercial cultivar 'BFP-605 Orange' (U.S. Plant Pat. No. 10,078) by having a somewhat lighter orange flower color, larger flowers that are flatter in shape (less cup-shaped) and medium green foliage, while 'BFP-605 Orange' has dark green foliage.

I claim:

1. A new and distinct cultivar of New Guinea *Impatiens* plant as shown and described herein.

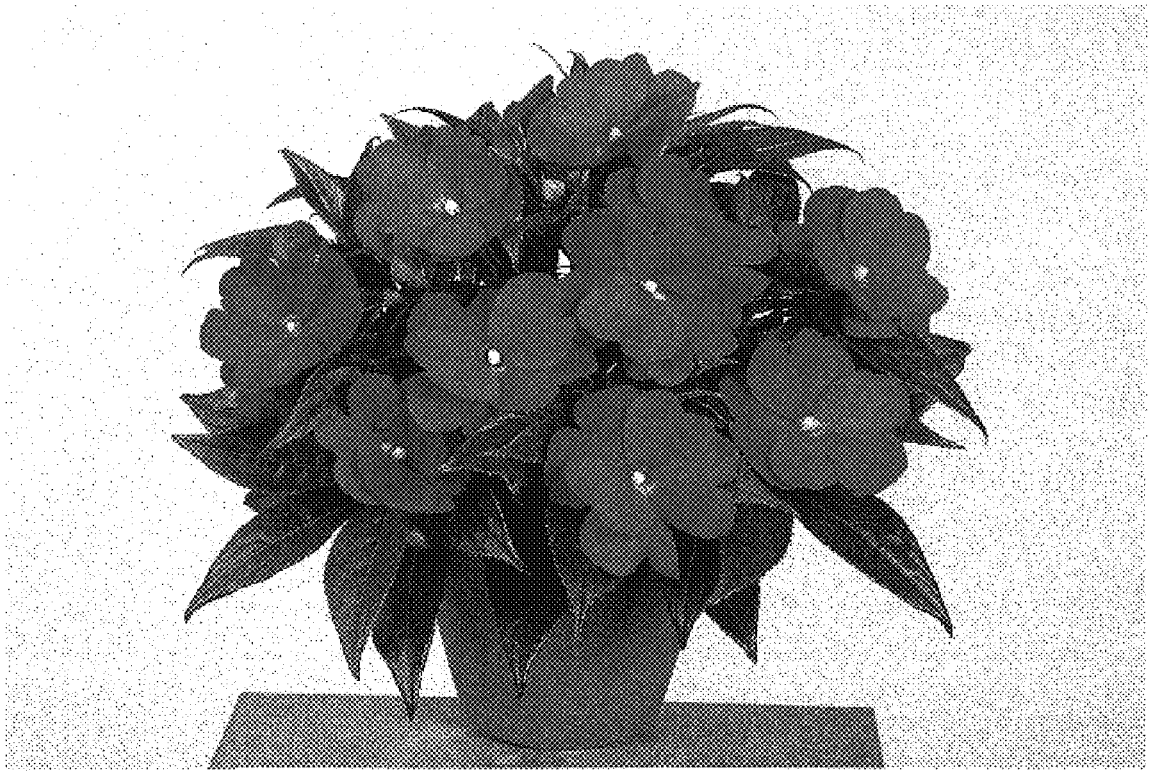

* * * * *